United States Patent [19]

Wallace

[11] 4,313,743

[45] Feb. 2, 1982

[54] ELECTROLYTIC MOISTURE INDICATOR INSIDE CHEMICAL CARTRIDGES

[76] Inventor: Richard A. Wallace, 7304 SW. 53rd Ave., Portland, Oreg. 97219

[21] Appl. No.: 132,854

[22] Filed: Mar. 24, 1980

[51] Int. Cl.$^3$ ............................................. B01D 53/04
[52] U.S. Cl. ............................... 55/275; 55/DIG. 33; 55/DIG. 34; 422/119; 422/120; 116/DIG. 25
[58] Field of Search ................. 55/163, 217, 274, 275, 55/DIG. 33, DIG. 34, DIG. 35; 200/61.04–61.07; 340/602; 116/DIG. 25; 422/119, 120; 210/96.1; 128/202.22

[56] References Cited

U.S. PATENT DOCUMENTS

| | | | |
|---|---|---|---|
| 2,621,753 | 12/1952 | Urdahl | 55/275 |
| 2,716,338 | 8/1955 | Blinn | 55/275 |
| 3,142,830 | 7/1964 | Patrick et al. | 55/275 |
| 3,773,044 | 11/1973 | Wallace | 55/275 |
| 3,944,916 | 3/1976 | Tillander | 200/61.05 |
| 4,154,586 | 5/1979 | Jones et al. | 55/274 |

FOREIGN PATENT DOCUMENTS 445457  5/1936  United Kingdom.

Primary Examiner—David L. Lacey
Attorney, Agent, or Firm—William A. King

[57] ABSTRACT

An electrolytic device adapted for mounting on the interior wall of a container housing sorbent chemicals for detection and display of moisture content. A sandwich or tab-type probe includes superhydroscopic $MgClO_4$ or $CaSO_4$ particles which resist electrical current flow when dry and have a higher affinity for moisture than the sorbent chemicals in cartridges or filters. Moisture intrusion is drawn to the anhydrous $MgClO_4$ or $CaSO_4$ particles changing their ohmic resistance and thereby enabling visual and nondestructive detection of the moisture intrusion into the container or cartridge. The probe is spaced away from the sorbent chemicals avoiding the transfer of mechanical stresses and any additional pressure drop through the sorbents, thereby permitting the device to be used in combination with a wide range of sealed containers and air filters.

3 Claims, 3 Drawing Figures

ELECTROLYTIC MOISTURE INDICATOR INSIDE CHEMICAL CARTRIDGES

BACKGROUND OF THE INVENTION

The present invention relates generally to accurately detecting slow intrusion of moisture into sealed containers and more particularly relates to the detection of progressive moisture damage to the housed, hydroscopic, granular chemicals such as charcoal, silica gel, potassium superoxide and HOPCALITE.

The electrolytic moisture indicator provides an instantaneous and rapid check on the effectiveness of the seal imposed on the emergency breathing rescue devices, as well as on the remaining sorbent life in air charcoal filters and high-pressure drying cartridges.

Known related art includes U.S. Pat. No. 3,773,044 granted to Richard A. Wallace on Nov. 20, 1973 and British Pat. No. 445,457 granted 9/21/1934.

The British Pat. No. 445,457 uses a hydroscopic substance; e.g., alkaline iodide, which restricts placement of its moisture-responsive element in that a flowable gas or vapor must traverse the hydroscopic substance in order to render the moisture-responsive element effective.

Various emergency breathing rescue devices have been presented with the more prevalent being Oxygen $KO_2$ SELF-RESCUERS, including the U.S. Bureau of Mines' combination 10 minute/60 minute breathing apparatus, Mine Safety Appliance's 60 minute self-breathing unit and Dragerwerk's oxygen self-rescuer device as well as filter self-rescuer containing HOPCALITE and charcoal. All self-contained oxygen breathing $KO_2$ devices and filter self-rescuers must have a useful storage life of at least five years.

Repetitive cyclic maintenance is required to monitor a multiplicity of oxygen self-rescuer canisters in order to detect moisture intrusion through the mechanical or vacuum seal imposed on their metal or plastic external case. This is especially true in mines where canisters must be stored for five-year periods. Moisture reacts with the hydroscopic, moisture-sensitive, oxygen-producing chemical, e.g., potassium superoxide or HOPCALITE, contained within the canisters and, at a given level, moisture intrusion will render such devices ineffectual.

These canisters are subjected to very damp environments (such as in mines which may approach 100% relative humidity) and are subjected to severe mechanical abuses. For example, miners will use their mechanically rugged metal or plastic housing cases as a readily accessible hammer or tool. In addition, these oxygen self-rescuer devices are also shaken considerably. Such high impact abuses over several years tend to insiduously damage (create tiny holes) in the mechanical or vacuum-proofing seal used to protect the hydroscopic oxygen-generating and filter chemicals. Further, government regulations require that oxygen self-rescuer canisters be daily tested for leakage or moisture intrusion.

At present, inherent deficiencies exist with the mechanical and vacuum seals imposed on the emergency self-rescuer breathing units. For instance, in oxygen self-rescuers with a mechanical seal, e.g., MSA's 60-minute breathing unit, a critical problem occurs with the rubber (NEOPRENE-type) gasket forming the mechanical seal. Over long periods of usage up to five years and thereafter, aging of the NEOPRENE rubber under pressure takes place resulting in harmful increased moisture permeability (i.e., slow moisture intrusion) through the gasket. This gradually deactivates the chemical sorbent. This moisture intrusion accelerates in the presence of pinholes or rubber slits, not readily observable by the naked eye. Similarly, for the oxygen self-rescuer with a vacuum-imposed seal, e.g., Dragerwerk's breathing unit, the vacuum tends to lose its effectiveness during prolonged usage ranging from three to six years. As a result, gradual moisture intrusion occurs and is absorbed by the potassium superoxide chemical, thereby slowly and insidiously decreasing its oxygen-generating property.

The present electrolytic moisture indicator resolves this critical moisture intrusion problem into chemical canisters and air filters.

SUMMARY OF THE INVENTION

In the present invention, moisture intrusion is detected by use of a superhydroscopic anhydrous salt (e.g., $MgClO_4$ or $CaSO_4$). The salt is placed in a metal perforated disc which is mounted to the interior wall of the canister to be monitored. Preferably, the electrolytic moisture indicator is placed in the inside dead space of the external housing. It is noted that the steel disc serves as an electrical ground.

The use of anhydrous superhydroscopic salts permits placement of the moisture-responsive electrolytic element at any convenient location within the cannister to be monitored because such salts attract even insidious moisture intrusion.

A metal probe is then mounted in the superhydroscopic salt, free of electrical conductive engagement with the perforated disc in order to permit resistance readings through the salt. A D.C. electrical resistance reading in ohms reflects the amount of moisture content or intrusion inside the canister, maximum electrical resistance when dry and minimum electrical resistance when wet. Such readings provide rapid verification of canister seal effectiveness.

Several limitations must be observed. The salt must have a higher degree of hydroscopicity (moisture-affinity) than the desiccant sorbent within the canister. These anhydrous drying salts have the ability to absorb moisture rapidly and progressively from the surrounding atmosphere, even low (less than 20 percent) relative humidities. Anhydrous magnesium perchlorate, calcium chloride, calcium sulfate, and lithium chloride exhibit in granular form the requisite powerful superhydroscopic property. These superhydroscopic salts absorb markedly more moisture (at least by four times on a basis of grams of water per gram of anhydrous superhydroscopic or drying salt) than the granular chemical sorbents, silica gel, alumina, activated charcoal, HOPCALITE, and potassium superoxide. Equally important, their rate of moisture sorption is at least four times faster than the chemical sorbents even at low relative humidities. Further, lead-ins must be vacuum tight, with virtually zero leakage. Moreover, given the adverse environment in which canisters are used, exposed leads, wires and engagement between the moisture detection device and the canister desiccant salts must be avoided.

A primary objective of the present invention is to provide a relatively uncomplex device for instantaneously detecting the amount of moisture intrusion into containers over several (1–5) years of usage in moisture-laden atmospheres.

Yet further objects, advantages and features will become apparent from the drawings and from the detailed description and claims which follow.

DETAILED DESCRIPTION OF THE INVENTION

Figure 1:
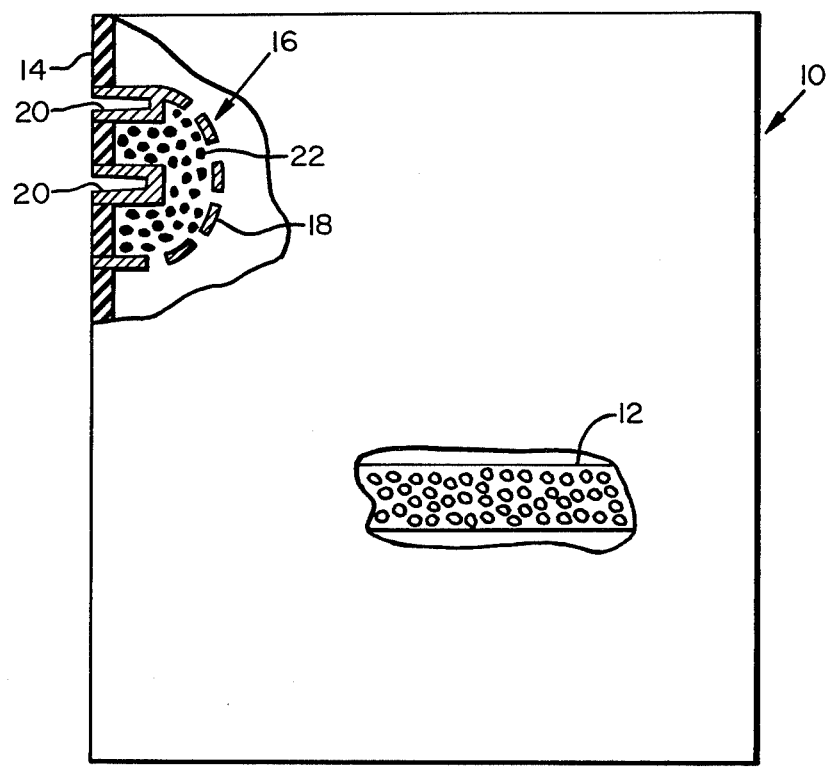
FIG. 1 is a partial breakaway cross section of an exemplary canister depicting the electrolytic detection device of the present electrolytic moisture indicator mounted on the inside wall (dead space) of the external housing.

Referring now to the drawings, numeral 10 refers generally to a container of the type housing a bed of hydroscopic sorbent chemicals 12 for purposes of oxygen generation, desiccation, filtering and the like.

Mounted in the wall 14 of container 10 is a moisture intrusion detection device referred to generally by numeral 16.

Device 16 includes a perforated metal disc 18 of suitable conductivity which houses a pair of female metal receptacles 20 and a pocket of superhydroscopic anhydrous $MgClO_4$ or $CaSO_4$ or $CaCl_2$ salts 22 arranged such that at least one of the receptacles is spaced away from the disc and electrically coupled with the other only through the superhydroscopic chemicals.

The granular, superhydroscopic salts 22 are of 20-50 mesh size, have maximum ohmic resistance (minimum electric conductivity) when dry and are extremely moisture loving, having a higher affinity, by at least four times, for moisture than the hydroscopic sorbent chemicals 12. Noteworthy examples for the hydroscopic sorbent canister and filter chemicals are potassium superoxide, charcoal, HOPCALITE, silica gel and alumina.

The receptacles are of predetermined cross section and preferably are of fused glass/metal weld construction, hermetically sealed into container wall 14. In most applications, the receptacles are of recessed probe lead-in construction so as to avoid exposed leads.

Moisture intrusion is detected by engaging the leads or probes of an ohmmeter 24 with receptacles 20. It being noted that the superhydroscopic anhydrous salts 22 will attract any moisture entering into container 10 and such moisture will decrease the resistivity (increase the conductivity) of the superhydroscopic chemical. Accordingly, by correlating the resistance reading to moisture intrusion (maximum resistance/minimum relative humidity to minimum resistance/maximum humidity), a decision can be made as to whether or not sufficient moisture has entered container 10 as would render the hydroscopic sorbent chemicals 12 ineffectual.

Figure 2:
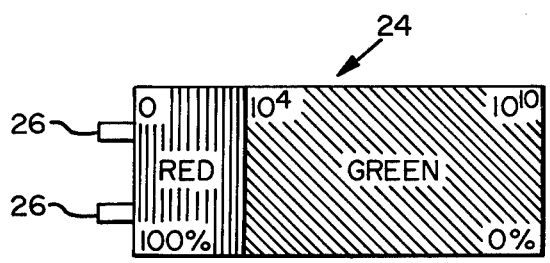
FIG. 2 is a schematic view of a preferred embodiment for the micro-ohmeter to be used in conjunction with the present moisture intrusion detection device.

Although virtually any ohmmeter could be employed with detection device 10, preferably micro-ohmmeter 24 of FIG. 2 should be employed. Here, the probes 26 are configured to readily mate the recessed receptacles 20 on the outside housing and the display portion of the ohmmeter is color coded (e.g., Red readings indicating high degree of moisture intrusion and Green readings indicating relatively safer levels of moisture intrusion). Thereupon, a go or no go visual indicator is instantly provided. Further, a very large number of canisters can be quickly checked using the single micro-ohmmeter.

EXAMPLE 1

FILTER SELF-RESCUER, Model FSR810 canisters were weighed, their seals broken, and then placed in their upright position in a large glass dessicator containing water in its bottom to provide a moisture-saturated atmosphere simulating a moisture-laden mine. In this fashion, a condition of slow moisture intrusion or leakage was provided over a prolonged period (two to four months). Periodically throughout the extended period, electrical ohmic resistance and weight readings were taken and recorded relative to the filter self-rescuers under test.

Figure 3:
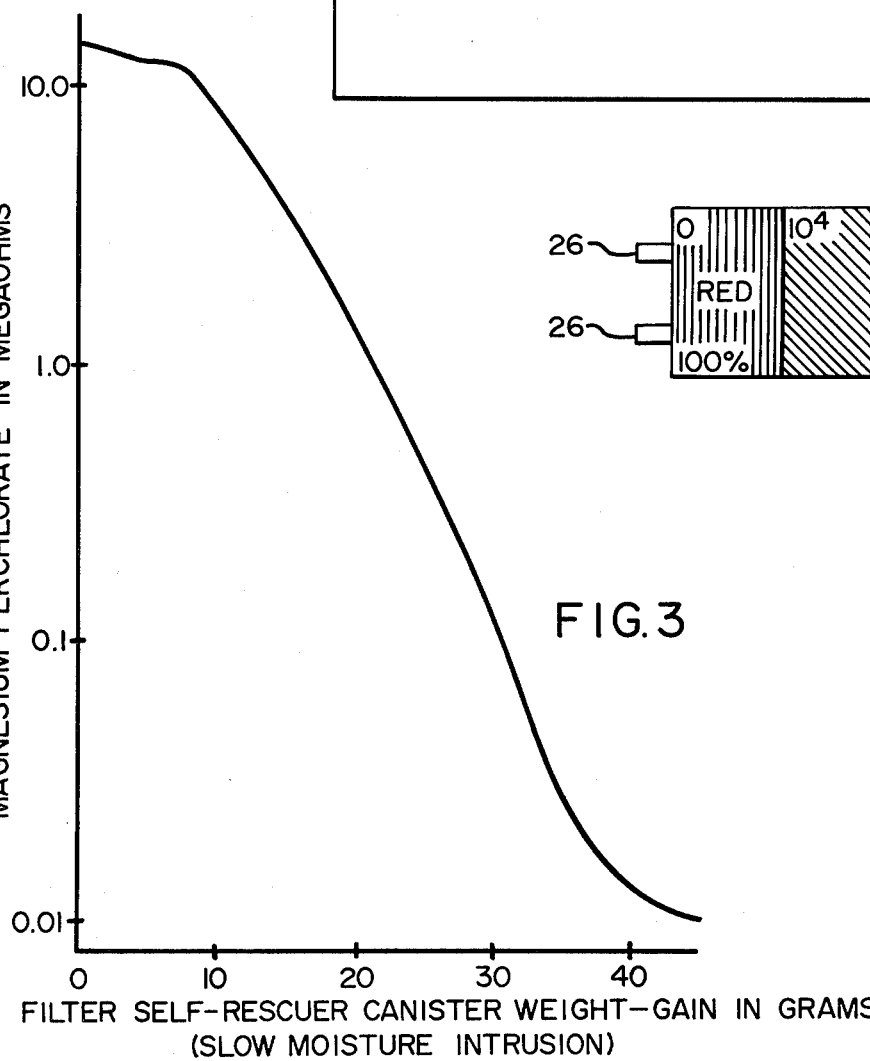
FIG. 3 represents typical experimental data obtained using the electrolytic moisture-detection device of FIG. 1.

FIG. 3 presents the experimental data derived from filter self-rescuer units and shows that:

1. ohmic resistance readings are a function of canister weight gain or moisture pickup during storage in the presence of a moisture-saturated air environment;
2. the knee of the ohmic resistance curve appears to occur at a canister weight gain of about 10 grams and thereafter falls rapidly;
3. a canister weight gain of about 22 grams causes the HOPCALITE-filled canister to fail the CO removal test;
4. a level of 10–12 grams of equilibrium moisture pickup for the subject canister is adequate prior warning for unsafe moisture intrusion; and
5. the present indicator offers rapid and relatively uncomplex methodology for detecting moisture intrusion in self-rescuer canisters with defective seals.

It is noted that the disc 18 of the test detector had about a two cm diameter, and consisted of a perforated steel disc housing anhydrous $MgClO_4$ in granular form and female recessed test probes. Disc 18 was attached to the inside wall of the plastic case in the upper dead space adjacent the upper portion of the filter self-rescuer.

EXAMPLE 2

The present electrolytic moisture indicator was attached to the inside of a Mine Safety Appliance's 60-minute oxygen self-rescuer rectangular canister. This self-rescuer canister contains about one kilogram of granular potassium superoxide sorbent and provides respiratory protection for the miner for at least 60 minutes. Its approximate dimensions are 27 cm in height, 20 cm in width, and 9 cm in depth. A ⅜ inch-wide NEOPRENE rubber gasket, HYDRIN-DuPont, forms the mechanical pressure seal protecting the moisture-loving potassium superoxide sorbent chemical from moisture intrusion. The oxygen self-rescuers are normally stored in the mine twenty-five feet from the miner.

The invented electrolytic moisture indicator is placed on the upper portion of the canister sidewall, facing the miner's chest. A fused glass/steel weld is made to hermetically seal the electrolytic indicator on the inside wall of the stainless steel case housing. Either magnesium perchlorate or calcium sulfate is used as the anhydrous superhydroscopic salt. The stainless steel case also serves as an electrical ground for the perforated steel disc or cup of the electrolytic moisture indicator.

The rubber gasket is removed and the same procedure is followed as is in Example 1. The ohmic resistance of the $MgClO_4$ declined progressively with canister exposure time. The initial ohmic resistance is very high, greater than $10^9$ ohms. After two months of moisture exposure, the ohmic resistance dropped to $10^4$ ohms. The electrolytic moisture indicator provided a rapid check for moisture intrusion into the oxygen self-rescuers having a faulty or defective rubber gasket seal.

For the other two types of potassium superoxide canisters, namely: (1) the NIOSH, U.S. Government, combined 10 minute/60 minute oxygen self-rescuer apparatus with a rubber gasket and a mechanical pressure seal; and (2) the Dragerwerk oxygen self-rescuer apparatus with a vacuum-imposed seal, similar results are determined. The electrolytic moisture indicator is mounted on the inside wall of the housing for each oxygen self-rescuer cartridge. The micro-ohmmeter offers a daily maintenance check for a large number of oxygen self-rescuers.

Although detection device 16 has been primarily described in combination with self-contained oxygen-generating potassium superoxide, apparatus as well as filter self-rescuers containing HOPCALITE and charcoal, it is significant to note that it also functions in combination with a wide range of sorbent filter devices, including but not limited to compressed air purifiers, granular charcoal filtration columns such as the ARC-ADSORPTIONSTECHNIK and related systems. There is therefore no intent or need to restrict the moisture detection device to an emergency oxygen-generating self-rescuer or filter self-rescuer.

For example, high-pressure drying cartridges contain a granular silica gel or alumina drying material and are used to remove moisture from compressed air flowing through air compressor systems. Such in-line drying cartridges are also used to dry, compress and transfer other gases such as oxygen (in e.g., a high-pressure oxygen transfer pump) refrigeration Freon gases, or organic vapors such as methane, gasoline and methyl chloride.

A primary difficulty with drying and air-purifying cartridges is that it is difficult to ascertain when sufficient moisture sorbent intrusion has occurred as would render these chemical cartridges ineffectual. Conversely, the moisture-intrusion detection device would provide an inexpensive and safe indication and measurement of moisture intrusion, thereby eliminating both the use of ineffectual filters and untimely removal of expensive, effectual filters. Yet another usage would be measuring water content of filter charcoal and/or silica gel systems in military vehicles such as tanks.

The terms and expressions which have been employed in the foregoing abstract and specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. In combination with a walled container having an interior air space and a predetermined quantity of hydroscopic sorbent chemicals in said air space having a first predetermined affinity for moisture, an electrolytic moisture detection device for detecting the occurrence and degree of moisture intrusion within said container and comprising:
    (a) an enclosure mounted in one of the walls of said container such that a portion of said enclosure extends into said air space in spaced relation with said hydroscopic sorbent chemicals;
    (b) said enclosure comprising perforated wall means which define a plurality of openings in said portion of said enclosure extending into said air space for permitting moisture to enter into said enclosure;
    (c) a plurality of superhydroscopic salt particles contained in said enclosure, each having a cross section greater than that of said openings, a second predetermined affinity for moisture greater than said first predetermined affinity and significantly high ohmic resistance when dry; and
    (d) a pair of electrically conductive terminals mounted in said enclosure in spaced apart relation and electrically insulated from one another, both of said terminals engaging said particles and being positioned and arranged with respect to said one wall to thereby define means for coupling said device with a D.C. voltage source and terminal to the other through said particles.

2. The combination of claim 1 wherein said superhydroscopic salt particles have a predetermined affinity for moisture greater than four times than that of said sorbent chemicals.

3. The combination of claim 1 wherein said superhydroscopic salt particles are an anhydrous superhydroscopic salt selected from the group consisting of magnesium perchlorate, calcium sulfate, calcium chloride and lithium chloride.

* * * * *